United States Patent
Barrett et al.

(10) Patent No.: US 9,676,028 B2
(45) Date of Patent: Jun. 13, 2017

(54) METHOD FOR PROCESSING CASTINGS

(71) Applicant: PCC Structurals, Inc., Portland, OR (US)

(72) Inventors: James Raphord Barrett, Milwaukie, OR (US); John Schleicher, Aloha, OR (US); James Ault, Vancouver, WA (US); David Pickett, Portland, OR (US)

(73) Assignee: PCC STRUCTURALS, INC., Portland, OR (US)

(\*) Notice: Subject to any disclaimer, the term of this patent is extended or adjusted under 35 U.S.C. 154(b) by 776 days.

(21) Appl. No.: 13/834,501

(22) Filed: Mar. 15, 2013

(65) Prior Publication Data

US 2014/0010706 A1    Jan. 9, 2014

Related U.S. Application Data

(60) Provisional application No. 61/668,967, filed on Jul. 6, 2012.

(51) Int. Cl.
| | |
|---|---|
| B22D 29/00 | (2006.01) |
| B22D 31/00 | (2006.01) |
| A61L 27/04 | (2006.01) |
| B24C 1/00 | (2006.01) |
| C22F 1/00 | (2006.01) |
| C22C 19/07 | (2006.01) |
| C22F 1/10 | (2006.01) |

(52) U.S. Cl.
CPC ............ *B22D 29/00* (2013.01); *A61L 27/045* (2013.01); *B22D 31/002* (2013.01); *B24C 1/00* (2013.01); *C22C 19/07* (2013.01); *C22F 1/00* (2013.01); *C22F 1/10* (2013.01); *A61L 2400/18* (2013.01); *A61L 2430/02* (2013.01)

(58) Field of Classification Search
CPC ......... B22D 29/00; B22D 31/002; C22F 1/00; C22F 1/02; A61L 27/04; A61L 27/045
USPC .............................. 164/76.1, 131; 623/23.53
See application file for complete search history.

(56) References Cited

U.S. PATENT DOCUMENTS

| | | | |
|---|---|---|---|
| 4,021,910 A | 5/1977 | Freeman, Jr. et al. | |
| 4,743,312 A | 5/1988 | Eridon et al. | |
| 5,706,881 A | 1/1998 | Grunstra et al. | |
| 5,913,354 A * | 6/1999 | Conroy ..................... | B08B 3/02 134/25.4 |
| 7,182,121 B1 * | 2/2007 | Viel .......................... | B22C 9/04 164/131 |
| 2006/0235536 A1 * | 10/2006 | Baliktay ................. | A61L 27/06 623/18.11 |

(Continued)

OTHER PUBLICATIONS

Callister Jr., "Materials Science and Engineering, An Intoduction", 2000, John Wiley & Sons, Inc., 5th Ed., p. 173.*

(Continued)

*Primary Examiner* — Kevin E Yoon
(74) *Attorney, Agent, or Firm* — Burris Law, PLLC

(57) ABSTRACT

A method of processing a casting is described. The method comprises removing a mold from a cast metal part without cold working surfaces of the cast metal part and thermally treating the cast metal part. The method can further comprise finishing the surfaces of the cast metal part after thermally treating such that any cold working of the surfaces of the cast metal part occurs after thermally treating such that no recast layer is formed in the cast metal part.

16 Claims, 5 Drawing Sheets

(56) References Cited

U.S. PATENT DOCUMENTS

2008/0241570 A1* 10/2008 Lawrynowicz ..... A61F 2/30767
428/577
2011/0066253 A1 3/2011 Langhorn et al.
2014/0193291 A1* 7/2014 Chan ........................ B22C 9/04
420/448

OTHER PUBLICATIONS

Zhuang et al., Effects of cooling rate control during the solidification process on the microstructure and mechanical properties of cast Co—Cr—Mo alloy used for surgical implants, Journal of Materials Science, vol. 24, pp. 381-388, Feb. 1989.*
F75 properties, https://www.dynacast.com/f-75-astm-hipped, Sep. 2016.*
ISR for PCT/US2013/049603 mailed on Feb. 13, 2014.

* cited by examiner

METHOD FOR PROCESSING CASTINGS

RELATED APPLICATIONS

This application claims priority under 35 U.S.C. §119(e) to U.S. Provisional Application No. 61/668,967, "IMPROVED METHOD FOR PROCESSING CASTINGS," filed Jul. 6, 2012, the entire contents of which are incorporated by reference.

FIELD

This disclosure relates generally to methods of processing castings. More specifically, this disclosure relates to methods of post-cast thermal treatment and finishing of castings.

BACKGROUND

The statements in this section merely provide background information related to the present disclosure and may not constitute prior art.

Sintered and non-sintered products are two categories of major joint orthopedic implants available on the market today. Sintered products can be subjected to high thermal process after completion of the casting process and are referred to as porous coated products. To make the porous coated products, high temperatures are used to create a metallurgical bond of porous beads to a cast substrate. Non-sintered products do not have a porous coating and can be generally referred to as cemented products.

Rough surfaces of implants can accelerate wear of joint-replacement implants. Therefore, implants are highly polished to reduce surface roughness of the implant. For example, roughness parameter Ra may be at least 8. Polishing can include mechanical and/or chemical polishing.

SUMMARY

According to one aspect of the present disclosure, a method of processing a casting is provided. The method can include removing a mold from a cast metal part without cold working surfaces of the cast metal part and thermally treating the cast metal part. The method can further include finishing the surfaces of the cast metal part after thermally treating such that any cold working of the surfaces of the cast metal part occurs after thermally treating such that no recast layer is formed in the cast metal part.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
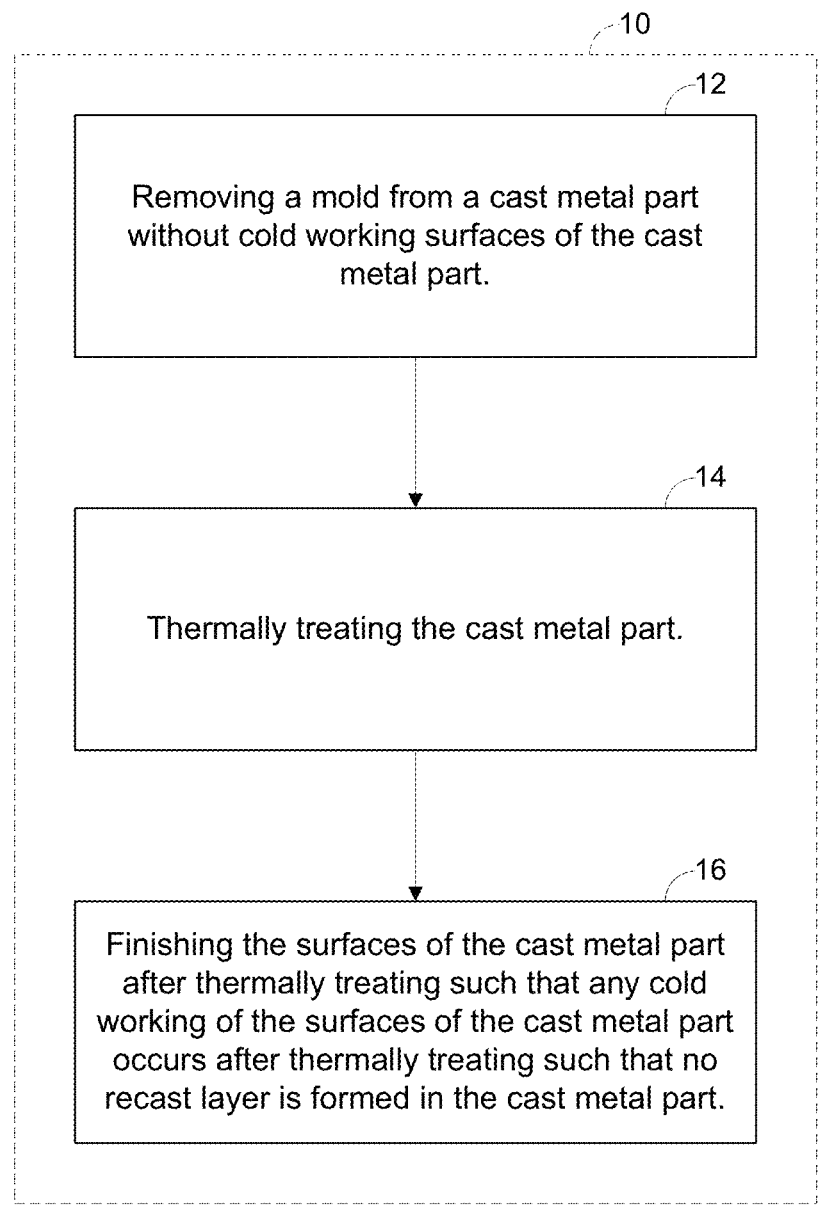
FIG. 1 is a flow diagram of an example method of processing a cast product compatible with certain aspects of the present disclosure.

The following description is merely exemplary in nature and is in no way intended to limit the present disclosure or its application or uses. It should be understood that throughout the description, corresponding reference numerals indicate like or corresponding parts and features.

The present disclosure generally relates to methods of processing castings. The castings made and used according to the teachings contained herein are described throughout the present disclosure in conjunction with cobalt-based investment castings in order to more fully illustrate the concept. The incorporation and use of methods in conjunction with other types of castings is contemplated to be within the scope of the disclosure.

According to certain aspects of the present disclosure, methods and processes are provided that are capable of eliminating a recast layer associated with castings such as cast F75 (CoCr) non-sintered orthopedic implants. Process changes to the routing of cast product are used to achieve the desired surface condition without a recast layer. Table I includes an exemplary composition of a F75 (CoCr) alloy.

TABLE I

| Element | Weight % |
| --- | --- |
| Chromium | 27-30 |
| Molybdenum | 5-7 |
| Nickel | <0.5 |
| Iron | <0.75 |
| Carbon | <0.35 |
| Silicon | <1 |
| Manganese | <1 |
| Tungsten | <0.2 |
| Phosphorus | <0.02 |
| Sulfur | <0.01 |
| Nitrogen | <0.25 |
| Aluminum | <0.1 |
| Titanium | <0.1 |
| Born | <0.01 |
| Cobalt | Balance |

Highly polished cast F75 (CoCr) orthopedic implants often need to have the recast surface layer removed prior to final polishing. The typical recast layer can be from 0.005" to 0.012" in thickness and can be removed by mechanical or chemical processes.

Metal on polymer or metal on metal cast F75 (CoCr) implants are often highly polished to reduce friction and wear in a biomechanical joint. Without this polishing, excess wear debris in the joint can lead to implant failure and may result in revisional surgeries.

The inventors discovered that cold working of the "as-cast" surfaces prior to thermal processing of the casting created the recast layer, through recrystallization of the as cast surfaces. Thermal processing can include various thermal treatments such as heat treatmenting or hot isostatic pressing (HIP). Furthermore, it was discovered that modifying process routing can eliminate "cold working" of the as cast surfaces prior to thermal processing of the cast implant. Castings can therefore be produced with no recast layer. For example, non-sintered cast F75 (CoCr) orthopedic implants can be provided without the recast layer.

The recast layer is a hard fine grained recrystallized surface that is removed prior to bright polishing of the implants articulating surface. If the recast layer is not removed, various anomalies may be in the polished surface that can create an undesired condition.

By eliminating the recast layer, certain benefits can be obtained including one or more of the following: reduced cost to manufacture products by eliminating machining/grinding, reduced finishing cost, reduce scrap, reduced lead times, reduced manufacturing cycle times, elimination of reprocessing after grinding, and elimination of expensive manufacturing equipment.

The recast layer can be removed on non-sintered (cemented) product. Sintered (porous coated) product may be subjected to thermal cycles after completion of the casting process and may result in recrystallization of the cast surface.

Cold working may be caused by a number of processes such as a cleaning operation, sandblast, grit blast or shot blast. Cold working can be identified by visual inspection of the as cast surfaces and can be mitigated by having an inspection operation verify that the castings have not been cold worked prior to advancing to the thermal processes. Once cold working has occurred, the product may not be able to have a no recast layer.

FIG. 1 is a flow diagram of an example method 10 of processing a cast product compatible with certain aspects described herein. In operational block 12, the method can include removing a mold from a cast metal part without cold working surfaces of the cast metal part. The mold can be formed by investment methods such as a lost wax process. The mold can be a ceramic mold or shell, and the ceramic mold can include silica and/or alumina. The method can include investment casting the cast metal part. For example, the cast metal part can be formed by disposing a molten metallic composition into the mold and a cooling the molten metallic composition to solidify the metallic composition to form the cast metal part. The cast metal part can be or comprise a cobalt-based material composition such that a largest constituent of the cast metal part is cobalt. However, the cast metal part can be other types of metals and alloys that may have a recast layer as a result of surface cold working prior to thermal treatment. The cast metal part may be polycrystalline. Grains of the cast metal part may be equiaxed, or the grains may be non-equiaxed or have irregular or different shapes and sizes. Furthermore, the cast metal part can be a non-sintered product.

The mold can be removed without cold working the surfaces of the cast metal part with, for example, chemical cleaning. An aqueous solution of one or more alkali hydroxides such as sodium hydroxide can be used to leech or remove the mold. Furthermore, mechanical removal of the mold may be eliminated or minimized to eliminate or minimize cold working of the surfaces of the cast metal part.

Cold working can include plastic deformation of the cast metal part. Therefore, the surfaces of the cast part may not be plastically deformed during the removal of the cast metal part from the mold. For example, the surfaces of the cast metal part may not be substantially cold worked or may essentially not be cold worked such that the surfaces are cold worked about 0%

In operational block 14, the method can further include thermally treating the cast metal part. Thermal treatment can include various procedures of heating to a temperature above room temperature and cooling back down depending on the composition of the cast metal part. The as cast microstructure of the cast metal part may not necessarily be the desired microstructure for the final product since a different microstructure may be desired to obtain particular properties (e.g., mechanical properties). The thermal treatment can be used to form a microstructure that is different from the as cast microstructure. For example, thermal treatment can be used to form a particular morphology of precipitates in a matrix.

The temperature and time at which the cast metal part is thermally treated can cause recrystallization of regions of the cast metal part that were cold worked prior to thermal treating. Therefore, the thermal treatment can include exposing the cast metal part to a temperature for a time that would cause recrystallization due to cold working. Since the method may not include cold working prior to thermal treatment, thermally treating the cast metal part may not cause recrystallization of the surface. The thermal treatment can include exposing the cast metal part to, for example, a temperature that is at least 50% from room temperature to the melting temperature of the cast metal part.

In operational block 16, the method can further include finishing the surfaces of the cast metal part after the thermal treatment such that any cold working of the surfaces of the cast metal part occurs after thermally treating such that no recast layer is formed in the cast metal part. The finishing may cause surfaces of the cast metal part to be cold worked. However, since the cast metal part may not experience further thermal treatment that would cause cold worked surfaces to recrystallize after finishing, the cold worked surfaces may not form a recast layer. Therefore, after all thermal treatments of the cast metal part, no recast layer may form in the cast metal part.

As described above, the recast layer may be formed as a result of recrystallization in regions that have been cold worked. Recrystallization can result in new grains forming. Therefore, the recast layer can have average grain size that is smaller than an average grain size prior to recrystallization or portions of the cast metal part without the recast layer. When a recast layer is not formed, an average grain size of the surface of the cast metal part can be about the same as an average grain size of an interior of the cast metal part. Since a recast layer can be prevented from forming, material from the surface of the cast metal part does not necessarily need to be removed. However, finishing processes, other than those to remove a recast layer, may also result in removal of some material from the surface of the cast metal part. However, the removal of material from the surface can be less than that is removed to remove a recast layer. Since the recast layer may have a thickness of 0.005 to 0.012 inches, the surface of the cast metal part without the recast layer may a thickness removed from the surface of the cast metal part that is less than about 0.005 inches or less than about 0.001 inches.

The finishing of the surfaces of the cast metal part can include at least one cleaning process selected from the group consisting of: sandblast, grit blast and shot blast. Furthermore, the method can include removing a gate of the cast metal part after thermal treating. Sandblasting, girt blasting, shot blasting and gate removal can each cause cold working of the surface of the cast metal part.

The cast metal part can be a component of various types. For example, a medical implant or an orthopedic implant can be manufactured by the methods described herein. As such, the cast metal part can be used as a medical implant or orthopedic implant.

The following specific embodiments are given to illustrate the design and use of methods according to the teachings of the present disclosure and should not be construed to limit the scope of the disclosure. Those skilled-in-the-art, in light of the present disclosure, will appreciate that many changes can be made in the specific embodiments which are disclosed herein and still obtain alike or similar result without departing from or exceeding the spirit or scope of the disclosure. One skilled in the art will further understand that any properties reported herein represent properties that are routinely measured and can be obtained by multiple different methods. The methods described herein represent one such method and other methods may be utilized without exceeding the scope of the present disclosure.

Trials were run to evaluate the removal of a recast layer and to compare the results of the modified no recast layer process to a non-modified process. Two development part numbers were established: 92840 as a non-modified casting and finishing process and 92841 as a modified process to eliminate the recast layer.

Figure 2:
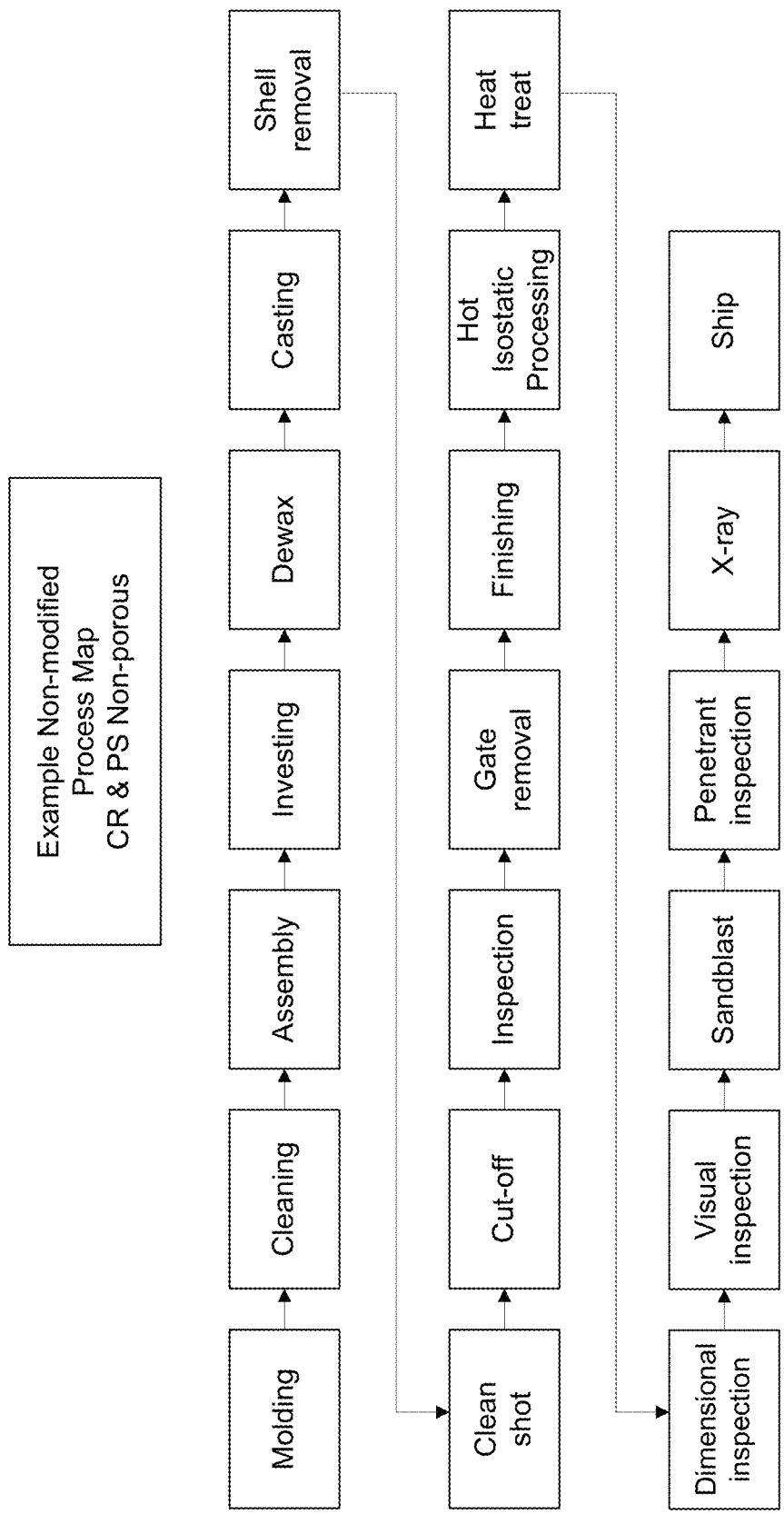
FIG. 2 is an example method of a non-modified casting and finishing process.

The non-modified casting and finishing process (92840) included the following steps: standard wax, standard shell, standard casting process, standard cleaning process, as cast metallography, standard thermal processes, standard finishing and non-destructive testing (NDT), and final metallography. A flow diagram of an example non-modified process is shown in FIG. 2.

Figure 3:
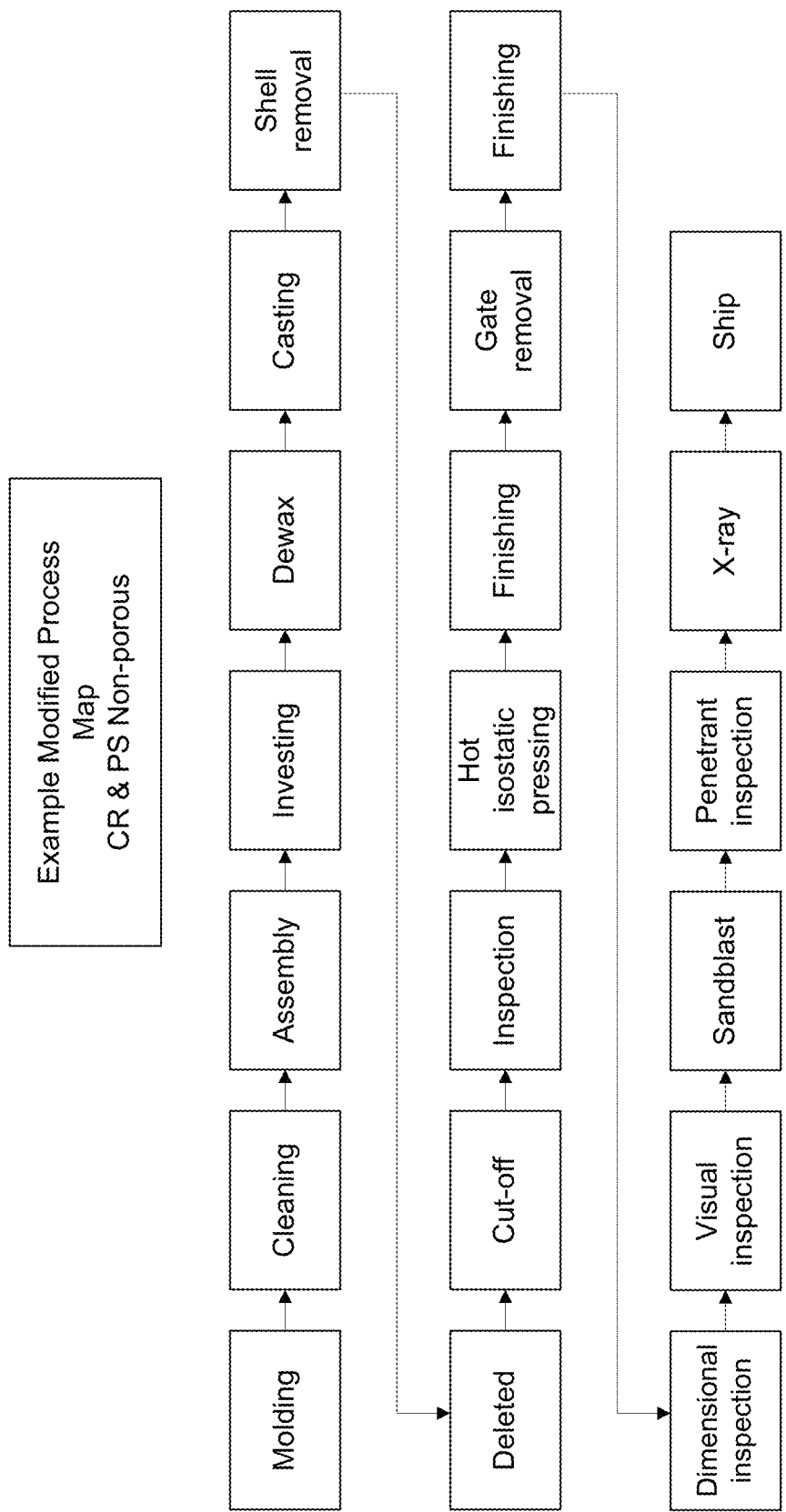
FIG. 3 is an example method of a modified casting and finishing process according to the teachings of the present disclosure.

The modified process to eliminate recast layer (92841) included the following steps: standard wax, standard shell, standard casting process, modified cleaning process, as cast metallography, standard thermal processes, modified gate grind, standard finishing and NDT, and final metallography. A flow diagram of an example modified process according to the teachings of the present disclosure is shown in FIG. 3.

Figure 4A:
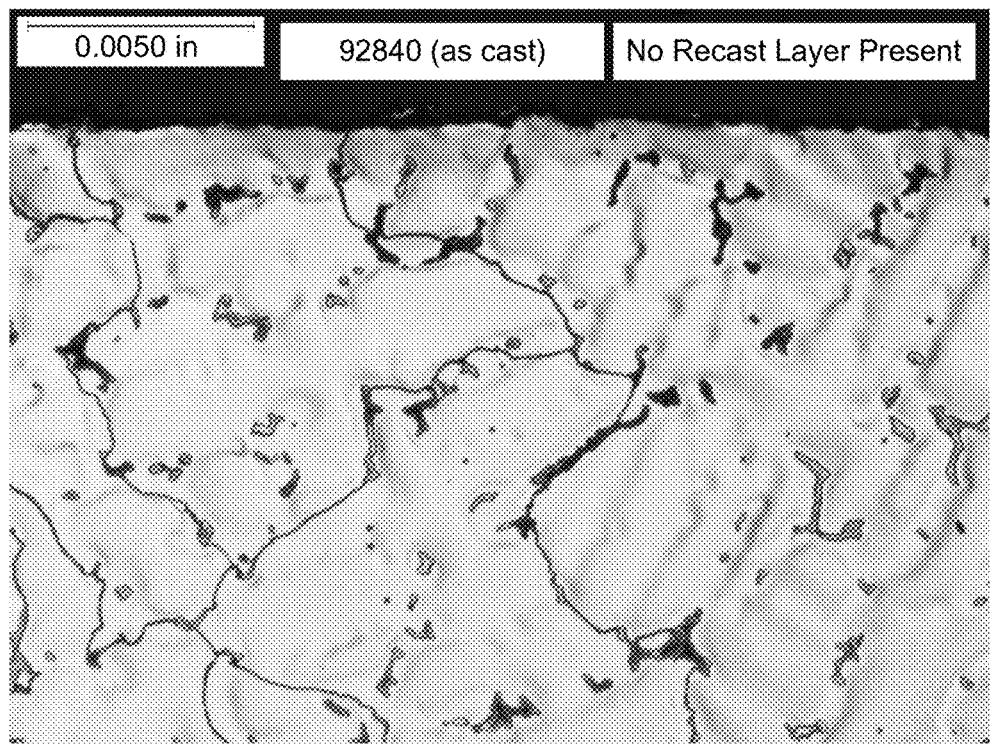
FIG. 4A is a micrograph of an example casting 92840 in an as cast condition according to the teachings of the present disclosure.
Figure 4B:
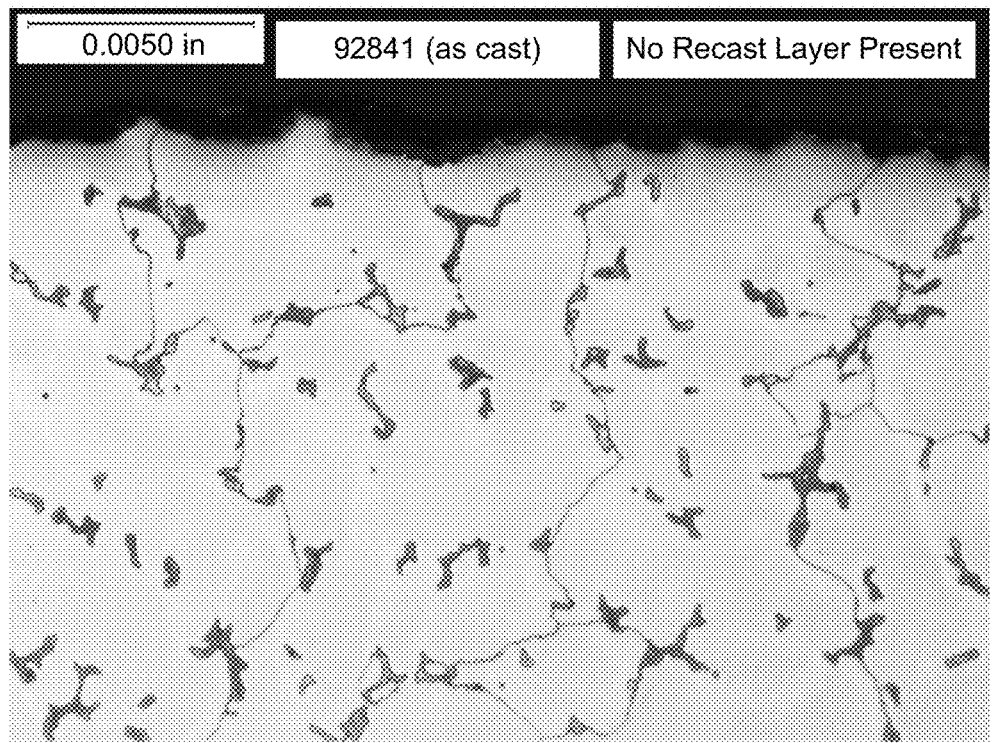
FIG. 4B is a micrograph of an example casting 92841 in an as cast condition according to the teachings of the present disclosure.
Figure 5A:
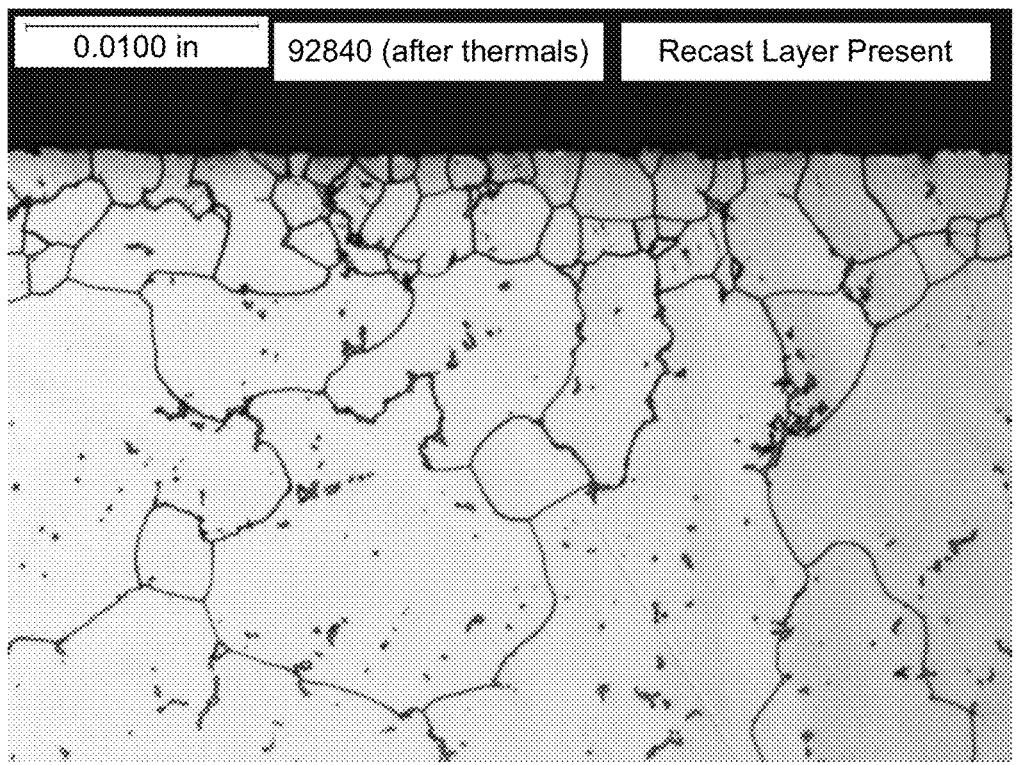
FIG. 5A is a micrograph of an example prior art casting 92840 after thermal treatments and finishing according to the teachings of the present disclosure.
Figure 5B:
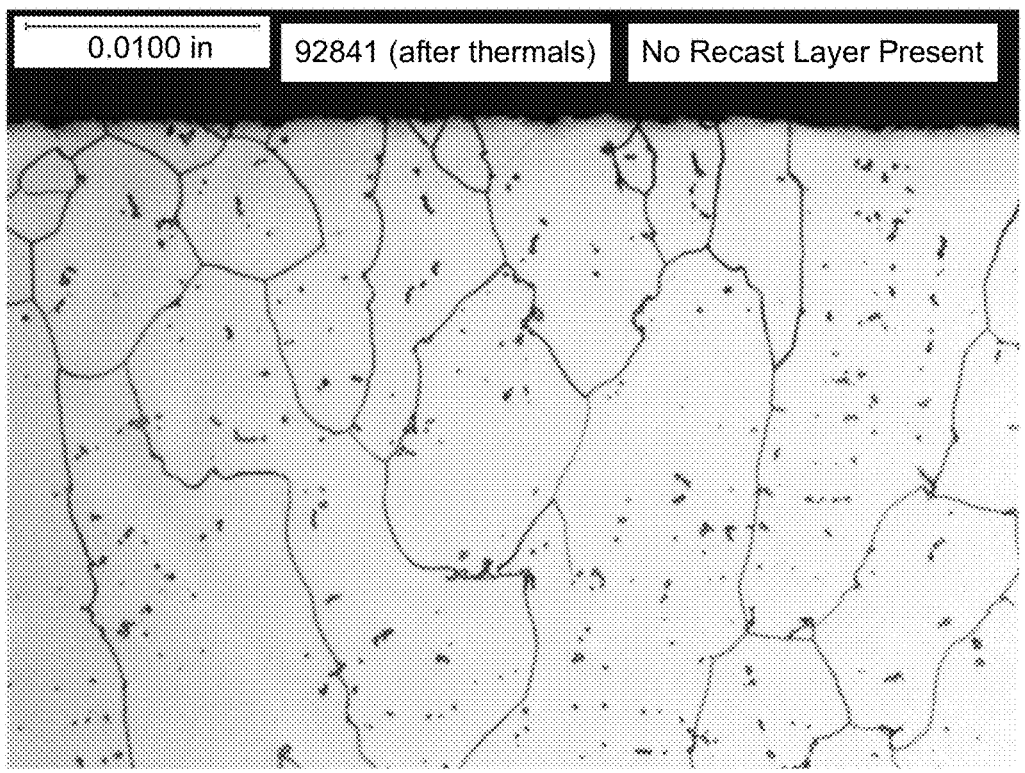
FIG. 5B is a micrograph of an example casting 92841 after thermal treatments and finishing according to the teachings of the present disclosure.

Castings produced from both processes were metallographicly evaluated as cast and after thermals in the final condition. The results can be seen in the FIGS. 4A-5B. The 92840 and 92841 samples contained no evidence of the recast layer in the as cast condition, as shown in FIGS. 4A and 4B, respectively. After final processing the non-modified process routing produced a casting with the typical recast layer present, as shown in FIG. 5A. However, the modified process produced a casting without any recast layer, as shown in FIG. 5B. After final processing, both samples received normal NDT process of visual and fluorescent penetrant inspection (FPI); no anomalies were discovered with either process. As such, non-sintered cast F75 (CoCr) orthopedic implants without the recast layer were able to be produced.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of processing a cast product to form a medical implant, the method comprising:
   forming a cast metal part comprising Cobalt-Chromium based alloy in a mold through a standard casting process;
   removing the mold from the cast metal part without cold working surfaces of the cast metal part by chemical cleaning, wherein the surface of the cast metal part is free from recrystallization of grains of the cast metal part;
   thermally treating the cast metal part; and
   finishing the surfaces of the cast metal part after thermally treating such that no recast layer is formed in the cast metal part.

2. The method of claim 1, wherein the cast metal part is polycrystalline.

3. The method of claim 2, wherein grains of the cast metal part are equiaxed.

4. The method of claim 1, wherein the thermally treating the cast metal part does not cause recrystallization of the surface.

5. The method of claim 1, wherein the finishing of the surfaces of the cast metal part comprises at least one cleaning process selected from the group consisting of: sandblast, grit blast and shot blast.

6. The method of claim 1, further comprising removing a gate of the cast metal part after thermal treating.

7. The method of claim 1, wherein the thermally treating comprises exposing the cast metal part to a temperature for a time that would cause recrystallization if the cast metal part had been cold worked prior to the thermal treating.

8. The method of claim 1, wherein, after the finishing of the surfaces of the cast metal part, the cast metal part is not exposed to a temperature for a time that would cause recrystallization due to the cold working of the surfaces of the cast metal part.

9. The method of claim 1, wherein the thermally treating comprises exposing the cast metal part to a temperature that is at least 50% from room temperature to the melting temperature of the cast metal part.

10. The method of claim 1, wherein a thickness of the surface of less than about 0.005 inches is removed from the surface of the cast metal part during finishing.

11. The method of claim 1, wherein the cast metal part comprises a cobalt-based material composition.

12. The method of claim 1, further comprising investment casting the cast metal part.

13. The method of claim 1, wherein the mold is a ceramic shell.

14. The method of claim 1, wherein the cast metal part is a non-sintered product.

15. The method of claim 1, wherein the cast metal part comprises Cobalt and a weight composition of 27-30% Chromium and less than 0.5% Nickel.

16. The method of claim 1, wherein the cast metal part comprises Chromium and a weight composition of at least 58.71% Cobalt and less than 0.5% Nickel.

* * * * *